United States Patent [19]

Shin et al.

[11] Patent Number: 6,054,450
[45] Date of Patent: Apr. 25, 2000

[54] HAIR-CARE COSMETIC COMPOSITIONS HAVING DANDRUFF FORMATION-SUPPRESSING EFFECT

[75] Inventors: Moon Sam Shin, Suwon; Sang Cho Choi, Seongmam; Yong Duk Kwak, Taejeon; Seong Hwan Seo, Yongin; Han Il Jeong, Anyang; Kyung Hee Seo, Seoul, all of Rep. of Korea

[73] Assignee: Pacific Corporation, Seoul, Rep. of Korea

[21] Appl. No.: 09/220,802

[22] Filed: Dec. 28, 1998

Related U.S. Application Data

[60] Continuation of application No. 09/100,753, Jun. 22, 1998, abandoned, which is a division of application No. 08/861,720, May 22, 1997, Pat. No. 5,886,031.

[30] Foreign Application Priority Data

| | | | |
|---|---|---|---|
| Jan. 27, 1997 | [KR] | Rep. of Korea | 97-2207 |
| Jan. 27, 1997 | [KR] | Rep. of Korea | 97-2208 |
| Mar. 22, 1997 | [KR] | Rep. of Korea | 97-9984 |
| May 7, 1997 | [KR] | Rep. of Korea | 97-17380 |

[51] Int. Cl.[7] ................................................. A61K 31/555
[52] U.S. Cl. ............................ 514/188; 514/558; 514/881
[58] Field of Search ..................................... 514/188, 558, 514/881

[56] References Cited

U.S. PATENT DOCUMENTS 3,236,733   2/1966   Karsten .

FOREIGN PATENT DOCUMENTS 268 911   6/1988   European Pat. Off. .

*Primary Examiner*—Rebecca Cook
*Attorney, Agent, or Firm*—Foley & Lardner

[57] ABSTRACT

Disclosed herein is hair-care cosmetic compositions comprising iodopropynyl butylcarbamate and/or a solution of zinc pyrithione in N-acyl ethylenediamine triacetate.

12 Claims, No Drawings

HAIR-CARE COSMETIC COMPOSITIONS HAVING DANDRUFF FORMATION-SUPPRESSING EFFECT

This application is a continuation of application Ser. No. 09/100,753, filed Jun. 22, 1998 abandoned; which is a divisional of Ser. No. 08/861,720, filed May 22, 1997 now U.S. Pat. No. 5,886,031.

BACKGROUND OF THE INVENTION

1. Field of the Invention

The present invention relates to hair-care cosmetic compositions having dandruff formation-suppressing effect. More particularly, it relates to hair-care cosmetic compositions containing iodopropynyl butylcarbamate and/or a solution of zinc pyrithione in N-acyl ethylenediamine triacetate.

2. Description of the Prior Art

In general, "dandruff" is a keratin-like mass caused from coagulation of dead cells stripped off from head skin and sebaceous secretion of head skin. Dandruff undergoes a change of its color into reddish gradually and forms a clear boundary from normal skin. Occasionally, it causes a skin disease accompanying itch and inflammation.

It has been known, though not clearly, that such dandruff may be caused by a hormone imbalance, a nutrition imbalance, nervous stresses, biochemical changes in the epidermal tissue resulting from an excessive multiplication of head epidermal cells, growths of microorganisms on the head skin and activity increase thereof, and inflammations due to air pollutions.

Particularly, *Pityrosporum ovlae*, which is a parasitic on dirty head skin, has been widely recognized as a main cause of dandruff formation. Multiplication and activity increase of this dandruff-causing microorganism make dandruff formation and itches more severe.

Hence, for the hair-care cosmetics for treatment and prevention of dandruffs and itch, it is essential to incorporate ingredients capable of suppressing multiplication and activity of the *Pityrosporum ovlae* effectively and returning abnormal metabolism of the head epidermal cells into normal condition.

Under this circumstance, the inventors have searched for materials having antibacterial activity against the dandruff-forming strain of *Pityrosporum ovlae*. As a result thereof, they found unexpectedly that MIC(Minimum Inhibition Concentration) of iodopropynyl butylcarbamate against *Pityrosporum ovlae* is very low. This compound, iodopropynyl butylcarbamate has been used as a general preservative due to sterilizing effect against bacteria and yeast. The inventors expected this compound to be available as an antibacterial agent and tried to apply it to the hair-care products, for example shampoo. As a result, they can constitute hair-care cosmetic compositions which show excellent suppressing effect on the dandruff-formation and itch.

Further, they reviewed the synergistic effect for the combinations of iodopropynyl butylcarbamate with zinc pyrithione, the latter being a typical antibacterial compound against *Pityrosporum ovlae*. A hair-care composition containing iodopropynyl butylcarbamate and zinc pyrithione, although it is slightly unstable due to low solubility of zinc pyrithione in water, showed synergistic effects in antibacterial activity against *Pityrosporum ovlae* and thereby dandruff reduction and itch-suppressing effect.

Furthermore, in order to solve the above problem associated with low solubility of zinc pyrithione in water, they studied the mechanism of dissolution of zinc pyrithione in water.

Zinc pyrithione has a spherical shape and a particle size of 0.3~10 μm. And it is substantially insoluble in water (10~20 ppm), ethanol(310 ppm) and most common organic solvents such as ethylene glycol, diethyl ether and isopropanol. Accordingly, it has been found difficult to formulate suitable cosmetic compositions containing zinc pyrithione in a dissolved form. In general, it has been accepted that such a low solubility of zinc pyrithione is due to heavy metal, zinc contained in molecule. In other words, the zinc pyrithione-dissolution needs a ligand capable of coordinate bonding with zinc contained in zinc pyrithione. As an appropriate example, amines such as diethanolamine and EDTA (ethylenediaminetetraacetic acid) have been employed. These amines have an unshared electron pair capable of coordinate bonding with zinc.(see U.S. Pat. No. 3,785,985 or U.S. Pat. No. 3,940,482).

These amines have pH 9 or high showing strong alkaline. Consequently, after dissolving zinc pyrithione, acid, for example citric acid should be added into the composition so as to adjust the pH value thereof neutral. However, by this pH change, the dissolved zinc pyrithione forms insoluble precipitates and the resulting composition becomes unstable. Further, these amines emit strong malodor, for example ammonia-like smell.

Under this circumstance, the present inventors have made research to provide a solution for the above problems associated with the low solubility of zinc pyrithione, such as instability of composition caused by precipitation of zinc pyrithione, and to find new material having unshared electron pair capable of coordinate bonding with zinc contained in zinc pyrithione and maintaining neutral in itself. As a result, they found N-acyl ethylenediamine triacetate to meet the above qualification.

SUMMARY OF THE INVENTION

Thus, an object of the invention is to provide hair-care cosmetic compositions having an antibacterial action against dandruff-causing microorganisms.

A further object of the invention is to provide a hair-care cosmetic composition containing iodopropynyl butylcarbamate, as an active ingredient.

A still further object of the invention is to provide a hair-care cosmetic composition containing iodopropynyl butylcarbamate and zinc pyrithione.

A still further object of the invention is to provide a hair-care cosmetic composition containing iodopropynyl butylcarbamate and a solution of zinc pyrithione in N-acyl ethylenediamine triacetate.

Also, a still further object of the invention is to provide a hair-care cosmetic composition containing a solution of zinc pyrithione in N-acyl ethylenediamine triacetate.

These and other objects will be apparent to those of ordinary skill in the art from the following disclosure.

DETAILED DESCRIPTION OF THE INVENTION

The present invention will be described in detail hereinafter.

Iodopropynyl butylcarbamate used in the hair-care cosmetic composition according to invention has the formula (I):

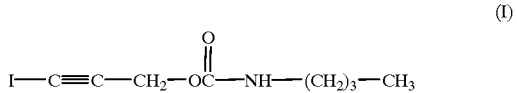

$$\text{I}-\text{C}\equiv\text{C}-\text{CH}_2-\text{O}\overset{\overset{\text{O}}{\|}}{\text{C}}-\text{NH}-(\text{CH}_2)_3-\text{CH}_3 \quad (I)$$

The various methods for preparing iodopropynyl butylcarbamate were described in detail in U.S. Pat. No. 4,259, 350, U.S. Pat. No. 4,841,088, U.S. Pat. No. 5,321,151 and U.S. Pat. No. 5,326,899. And it has been applied as a preservative for wood materials (see U.S. Pat. No. 4,323,602 and U.S. Pat. No. 4,977,186).

The present inventors revealed in the first place that iodopropynyl butylcarbamate exhibits an antibacterial action against *Pityrosporum ovlae* and found its action to be very strong. Furthermore, they reviewed its applicability to formulate hair-care products.

Iodopropynyl butylcarbamate has a low solubility in water, but good solubility in ionic or non-ionic surfactants. Specially, it shows a high solubility in alcohols or glycol derivatives. Based on this fact, they concluded that iodopropynyl butylcarbamate can be applied to and formulated into hair-care products. Also, iodopropynyl butylcarbamate is very stable at a temperature of 70~80° C. and pH 4~10. And, comparing with zinc pyrithione, it is very advantageous over zinc pyrithione in the light of safety and toxicity. It has an Acute Oral $LD_{50}$(rats) of 1470 mg/kg, while zinc pyrithione has Acute Oral $LD_{50}$(rats) of 354 mg/kg. Based on these facts, the hair-care composition according to the present invention may comprise iodopropynyl butylcarbamate in an amount of 0.001~20% by weight, and preferably of 0.001~10% by weight based on total weight of the composition.

In order to increase adsorption of iodopropynyl butylcarbamate to the head skin, the composition may further contain one or more adsorption-accelerating agents selected from guar hydroxypropyl trimonium chloride, polyquaternium-7, polyquaternium-10, and urea, in an amount of 0.001~10% by weight based on total weight of the composition.

Further, zinc pyrithione(zinc salt of 1-hydroxy-2(1H) pyridinethione) incorporated in the present composition is very effective as a dandruff controlling agent represented by the formula (II):

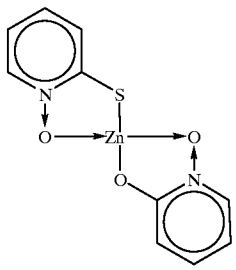

(II)

It has a spherical shape and a particle size of 0.3~10 μm. Its solubility in water at 25° C. is only about 15 ppm. According to the present invention, for the purpose of attaining a synergistic effect, the zinc pyrithione may be incorporated into hair-care cosmetic compositions in an amount of 0.001~5% by weight based on total weight of the composition.

In order to increase solubility of zinc pyrithione, the composition according to the present invention may comprise one or more conventional chelating agents. Examples thereof may include, but not limited thereto, EDTA (ethylenediamine tetraacetic acid), diethylenetriamine pentaacetic acid, nitroyltriacetic acid, cyclohexanediamine tetraacetic acid, triethanolamine ethylenediamine tetraacetic acid, tetraethylenetriamine, ethylenediamine, diethylenetriamine diethyltriamine and their salts. The chelating agent(s) may be incorporated in an amount of 0.001~10% by weight based on total weight of the composition.

More specially, when the composition comprises zinc pyrithione, it is more advantageous that zinc pyrithione may be incorporated in a solution form obtained by dissolving zinc pyrithione with N-acyl ethylenediamine triacetate. N-acyl ethylenediamine triacetate(hereinafter referred to as N-acyl-EDTA) is chelating surfactant which may be synthesized chemically from EDTA and acyl group-containing surfactant (Crudden J. J. and et al, Inform, Vol. 6, No. 6, October 1995). It can be represented by formula (III) and has, in the molecule, EDTA-structure as well as a surfactant-structure:

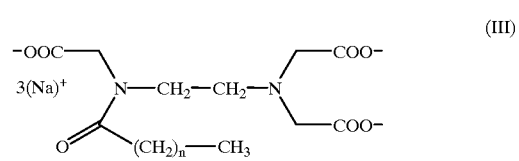

(III)

wherein, n is an integer from 10 to 18, inclusive.

N-Acyl-EDTA has unshared electron pair capable of coordinate bonding with zinc contained in zinc pyrithione and maintain neutral in itself. It shows foaming and cleansing actions as well as serves as a chelating agent which blocks metal.

Special examples of N-Acyl-EDTA are sodium lauroyl ethylenediamine triacetate, sodium myristoyl ethylenediamine triacetate, sodium palmitoyl ethylenediamine triacetate, sodium stearoyl ethylenediamine triacetate or sodium cocoyl ethylenediamine triacetate. The N-acyl-EDTA chelating surfactant may be incorporated in an amount of 0.01~20% by weight based on total weight of the composition.

Zinc pyrithione can be dissolved by forming coordinate bonds with N-acyl-EDTA. Zinc pyrithione dissolved has a particle size of 0.0001~0.001 μm. Accordingly, an unit surface area of zinc pyrithione increases and amount to be adsorbed to the skin increases. Further, because its particle size is significantly small, its penetration through the skin barrier increases. In experiments using Adhesive Scatch Tape Stripping Method to determine the adsorption into the head skin, in case of the dissolved zinc pyrithione, zinc pyrithione was detected at all of the 1st through 5th strippings, while the insoluble zinc pyrithione was not detected from 2nd stripping. Due to such increased adsorption and penetration, a composition containing zinc pyrithione solution exhibits an increased antidandruff effect.

The hair-care compositions according to the present invention may be formulated into, for example, shampoos, rinses, hair-conditioners, hair-tonics, hair-treatment creams and lotions, and the like. Each composition of these formulations may, it necessary, contain appropriate vehicles and various additives. The kind and amount of these ingredients are not critical and can be selected appropriately and easily by those of ordinary skill in the art.

Following description will be given as to these cosmetic bases and additives, as an example of shampoo.

Shampoos may contain synthetic surfactants, preservatives, thickeners and viscosity controllers, pH adjusters, perfumes, dyes, hair conditioning components and distilled water. Suitable synthetic surfactants may be selected from the group consisting of anionic, amphoteric, nonionic and cationic surfactants, and may be incorporated in amount of 10~70% by weight, preferably 10~30% by weight.

Examples of suitable anionic surfactants may include alkyl or alkylether sulfates represented by formula (IV):

$$RO(C_2H_4O)_nSO_3M \qquad (IV)$$

wherein, R is an alkyl group having 10~22 carbon atoms, n is 0 or an integer of 1~4 inclusive and M is water-soluble cation such as ammonium, sodium and triethanolamine. Preferable examples are an alkyl or an alkylether sulfates wherein R is an alkyl group having 12~16 carbon atoms. More particularly, it may be exemplified by sodium lauryl sulfate, ammonium lauryl sulfate, triethanolamine lauryl sulfate, polyoxyethylene sodium lauryl sulfate, or polyoxyethylene ammonium lauryl sulfate.

Examples of suitable amphoteric surfactants may include alkyl betaines and alkyl amidopropyl betaines represented by formulae (V) and (VI), respectively:

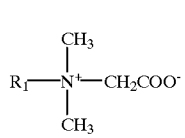

(V)

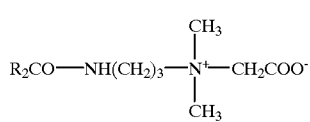

(VI)

wherein, R is an alkyl group having 8~18 carbon atoms and $R_2CO$ is an alkoxy group having 8~18 carbon atoms. More particularly, it may be exemplified by cocodimethyl carboxymethyl betaine, lauryldimethyl carboxymethyl betaine, lauryldimethyl α-carboxyethyl betaine, cetyldimethyl carboxymethyl betaine, and cocoamindopropyl betaine.

Examples of suitable nonionic surfactants may include alkanolamides and alkylamineoxides represented by formulae (VII) and (VIII), respectively:

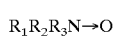 (VII)

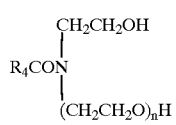 (V)

wherein, $R_1$ is an alkyl group having 8~18 carbon atoms, $R_2$ and $R_3$ are same or different, an alkyl group having 1~3 carbon atoms, and $R_4CO$ is alkoxy group having 8~16 carbon atoms, and n is 0 or 1 inclusive. More particularly, it may be exemplified by lauryl diethylamine oxide, alkyl dimethylamine oxide derived from coconut oil, diethanolamide of lauric acid, diethanolamide of coconut fatty acid and monoethanolamide of coconut fatty acid.

The above-mentioned surfactants may be incorporated in single or as mixtures thereof.

The hair-care cosmetic compositions according to the present invention can be used in a conventional manner and how-often can be determined depending on the skin condition or tastes of the user.

PREFERRED EMBODIMENTS OF THE INVENTION

The present invention will be illustrated in more detail by way of the following Examples. The following Examples are merely illustrative and it should be understood that the present invention is not limited to these Examples.

EXAMPLES 1~8 AND COMPARATIVE EXAMPLES 1~2

Shampoo

| Ingredients | C. Examples 1 | C. Examples 2 | Examples 1 | Examples 2 | Examples 3 | Examples 4 | Examples 5 | Examples 6 | Examples 7 | Examples 8 |
|---|---|---|---|---|---|---|---|---|---|---|
| 1. Polyoxyethylene lauryl ether sodium sulfate (26%) | 30.0 | 30.0 | 30.0 | 30.0 | 30.0 | 30.0 | 30.0 | 30.0 | 30.0 | 30.0 |
| 2. Sodium lauryl sulfate (28%) | 15.0 | 15.0 | 15.0 | 15.0 | 15.0 | 15.0 | 15.0 | 15.0 | 15.0 | 15.0 |
| 3. Lauryl diethanol amide | 4.5 | 4.5 | 4.5 | 4.5 | 4.5 | 4.5 | 4.5 | 4.5 | 4.5 | 4.5 |
| 4. Propylene glycol | 0.5 | 0.5 | 0.5 | 0.5 | 0.5 | 0.5 | 0.5 | 0.5 | 0.5 | 0.5 |
| 5. Methyl p-hydroxy benzoate | 0.2 | 0.2 | 0.2 | 0.2 | 0.2 | 0.2 | 0.2 | 0.2 | 0.2 | 0.2 |
| 6. Pigment | q.s | q.s | q.s | q.s | q.s | q.s | q.s | q.s | q.s | q.s |
| 7. Perfume | q.s | q.s | q.s | q.s | q.s | q.s | q.s | q.s | q.s | q.s |
| 8. Citric acid | q.s | q.s | q.s | q.s | q.s | q.s | q.s | q.s | q.s | q.s |
| 9. Iodopropynyl butylcarbamate | — | — | 1.0 | 1.0 | 1.0 | 0.3 | 0.5 | 1.0 | — | — |
| 10. Polyquaternium-7 | — | — | — | 0.5 | — | — | 0.5 | — | — | — |
| 11. Zinc pyrithione(48% of suspension) | — | 1.0 | — | — | 1.0 | — | — | — | — | — |
| 12. Zinc pyrithione(powder) | — | — | — | — | — | 0.3 | 0.5 | 1.0 | 1.0 | 1.0 |
| 13. Sodium lauroyl ethylenediamine triacetate | — | — | — | — | — | 1.5 | 2.5 | 5.0 | 5.0 | 5.0 |
| 14. EDTA-2Na | 1.5 | 1.5 | — | — | 1.5 | — | 1.5 | — | — | 0.5 |
| 15. Distilled water | | | | | to 100 | | | | | |

EXPERIMENTAL EXAMPLE 1

Antibacterial Action

The culture of the test microorganisms was streaked onto agar plates containing various concentrations of the shampoos prepared in Examples and Comparative Examples, and then were cultivated under an aerobic condition for 2 days. Growth of the microorganism was observed and MIC (Minimum Inhibition Concentration) against the test microorganism was determined. The results are summarized in Table 1.

1. Test microorganism:
*Pityrosporum ovlae* ATCC 12087
2. Culture medium:
Blood agar medium(Blood agar base+5% final concentration of blood), BHI agar

TABLE 1

| | MIC ($\mu$g/ml) | | | | | | | | |
|---|---|---|---|---|---|---|---|---|---|
| | C. Examples | | Examples | | | | | | |
| | 1 | 2 | 1 | 2 | 3 | 4 | 5 | 6 | 7 | 8 |
| *Pityrosporum ovlae* | >10000 | 5.87 | 1.08 | 0.89 | 0.045 | 2.14 | 0.22 | 0.025 | 1.88 | 0.85 |

EXPERIMENTAL EXAMPLE 2

Inhibition of Growth of *P. ovlae*

This test was performed using Skin Disc Diffusion Method. First, the culture of the test microorganism (*Pityrosporum ovlae* ATCC 12087) was streaked onto agar plates and then were cultivated under an aerobic condition at a temperature of 37° C. for 2 days. After skin discs were sterilized with 70% of ethanol, it was treated with 1/10-dilution of the shampoos prepared in Examples and Comparative Examples, and then washed with distilled water. Skin discs thus treated were placed onto the above agar plates. After allowing to stand for 48 hours at a temperature of 37° C., inhibition zones were measured. The inhibition zone was defined as a clear circular zone where the test microorganism in the agar plate died by inhibition of the material(shampoo dilution) treated on the skin disc. This measurement was repeated 3 times and averaged. The values in Table 2 are the difference between the radius of the inhibition zone and the radius of the skin disc.

TABLE 2

| | Mean Inhibition Zones(min) | | | | | | | | |
|---|---|---|---|---|---|---|---|---|---|
| | C. Examples | | Examples | | | | | | |
| | 1 | 2 | 1 | 2 | 3 | 4 | 5 | 6 | 7 | 8 |
| Inhibition Zones (mm) | 0.00 | 10.88 | 18.55 | 20.63 | 30.79 | 27.4 | 30.46 | 38.59 | 15.65 | 17.66 |

EXPERIMENTAL EXAMPLE 3

Dandruff Formation-reducing Action

In order to evaluate and compare dandruff formation-reducing action of the shampoos prepared in Examples and Comparative Examples, these shampoos were applied to 10 Groups each consisting of 8 males aging 19 to 45 years, for one month.

Before this test, they washed hair with the conventional shampoo, and dandruff accumulated for 3 days were gathered and weighed. In turn, each group washed hair with the shampoo of Example or of C. Example every 3 days for one month, and thereafter, dandruff accumulated for 3 days was collected and weighed. At this time, the accumulated dandruff was collected from the head skin using vacuum suction apparatus. Dandruff-reduction was determined by following formula:

Dandruff formation-reduction(%)={(weight(mg) of dandruff before test)−(weight(mg) of dandruff after 1 month)}÷{weight(mg) of dandruff before test}×100

TABLE 3

| | C. Examples | | Examples | | | | | | | |
|---|---|---|---|---|---|---|---|---|---|---|
| | 1 | 2 | 1 | 2 | 3 | 4 | 5 | 6 | 7 | 8 |
| Dandruff reduction (%) | 1.03 | 45.8 | 59.8 | 65.3 | 93.3 | 57.8 | 73.5 | 97.8 | 73.5 | 90.7 |

As shown in Tables 1 to 3, shampoos containing iodopropynyl butylcarbamate(Example 1) were more effective in inhibiting the growth of *P. ovlae* and in suppressing the formation of dandruff, compared with shampoo containing the dispersed zinc pyrithione(C. Example 2).

Also, shampoo containing the dissolved zinc pyrithione(Example 7) was more effective in inhibiting growth of *P. ovlae* and in suppressing the formation of dandruff, compared with shampoo containing the dispersed zinc pyrithione(C. Example 2). This may be in that the dissolved zinc pyrithione exists in the form of molecule, while the dispersed zinc pyrithione exists in the form of particle.

EXPERIMENTAL EXAMPLE 4

Stability of the Composition

In order to examine stability of the shampoos prepared in Examples and C. Examples, these shampoos were stored at 0° C. for 3 months and at 25° C. for 6 months, and precipitation was observed. The results are shown in Table 4.

TABLE 4

| | C. Example | | Examples | | | |
|---|---|---|---|---|---|---|
| | 1 | 2 | 3 | 6 | 7 | 8 |
| 0° C., 3 months | X | ○ | ○ | X | X | X |
| 25° C., 6 months | X | ◉ | ○ | X | X | X |

Note)
◉: Serious precipitation
○: Slight precipitation
X: No precipitation

As shown in Table 4, the precipitates formed in shampoo of C. Example 2 may be that of zinc pyrithione by pH change. That is to say, zinc pyrithione dissolved or dispersed using the alkali may be precipitated by adding citric acid.

What is claimed is:

1. A method for preventing precipitation of zinc pyrithione in an anti-dandruff composition comprising zinc pyrithione, comprising:

incorporating zinc pyrithione into said composition in solution form obtained by dissolving zinc pyrithione with a zinc pyrithione-dissolving agent represented by formula III:

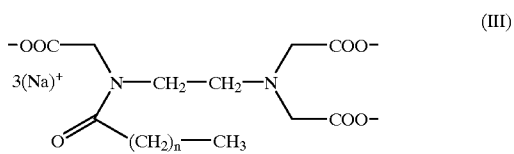

wherein, n is an integer from 10 to 18,
in order to increase the solubility of zinc pyrithione.

2. The method according to claim 1, wherein said zinc pyrithione-dissolving agent is selected from the group consisting of sodium lauroyl ethylenediaminetriacetate, sodium myristoyl ethylenediaminetriacetate, sodium palmitoyl ethylenediaminetriacetate, sodium stearoyl ethylenediaminetriacetate and sodium cocoyl ethylenediaminetriacetate.

3. The method of claim 1, wherein said composition further comprises one or more chelating agents selected from the group consisting of ethylenediaminetetraacetic acid, diethylenetriaminepentaacetic acid, nitrilotriacetic acid, cyclohexanediaminetetraacetic acid, triethanolamine ethylenediaminetetraacetic acid, tetraethylenetriamine, ethylenediamine and diethylenetriamine, or a salt thereof.

4. A method for reducing dandruff formation, comprising;
   applying to a subject in need thereof, a composition comprising zinc pyrithione and an effective amount of a zinc pyrithione-dissolving agent represented by formula III:

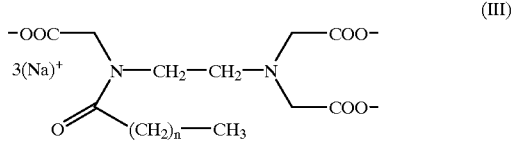

wherein, n is an integer from 10 to 18.

5. The method according to claim 4, wherein said zinc pyrithione-dissolving agent is selected from the group consisting of sodium lauroyl ethylenediaminetriacetate, sodium myristoyl ethylenediaminetriacetate, sodium palmitoyl ethylenediaminetriacetate, sodium stearoyl ethylenediaminetriacetate and sodium cocoyl ethylenediaminetriacetate.

6. The method of claim 4, wherein said composition further comprises one or more chelating agents selected from the group consisting of ethylenediaminetetraacetic acid, diethylenetriaminepentaacetic acid, nitrilotriacetic acid, cyclohexanediaminetetraacetic acid, triethanolamine ethylenediaminetetraacetic acid, tetraethylenetriamine, ethylenediamine and diethylenetriamine, or a salt thereof.

7. A method for stabilizing an anti-dandruff composition comprising zinc pyrithione comprising:

adding to said composition an effective amount of a zinc pyrithione-dissolving agent represented by formula III:

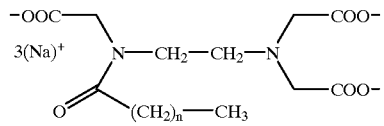
(III)

wherein, n is an integer from 10 to 18.

8. The method according to claim 7, wherein said zinc pyrithione-dissolving agent is selected from the group consisting of sodium lauroyl ethylenediaminetriacetate, sodium myristoyl ethylenediaminetriacetate, sodium palmitoyl ethylenediaminetriacetate, sodium stearoyl ethylenediaminetriacetate and sodium cocoyl ethylenediaminetriacetate.

9. The method of claim 7, wherein said composition further comprises one or more chelating agents selected from the group consisting of ethylenediaminetetraacetic acid, diethylenetriaminepentaacetic acid, nitrilotriacetic acid, cyclohexanediaminetetraacetic acid, triethanolamine ethylenediaminetetraacetic acid, tetraethylenetriamine, ethylenediamine and diethylenetriamine, or a salt thereof.

10. An antidandruff composition comprising:
zinc pyrithione and a zinc pyrithione-dissolving agent represented by formula III:

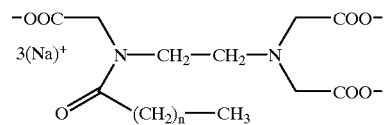
(III)

wherein, n is an integer from 10 to 18.

11. The composition according to claim 10, wherein said zinc pyrithione-dissolving agent is selected from the group consisting of sodium lauroyl ethylenediaminetriacetate, sodium myristoyl ethylenediaminetriacetate, sodium palmitoyl ethylenediaminetriacetate, sodium stearoyl ethylenediaminetriacetate and sodium cocoyl ethylenediaminetriacetate.

12. The composition of claim 10, wherein said composition further comprises one or more chelating agents selected from the group consisting of ethylenediamine-tetraacetic acid, diethylenetriaminepentaacetic acid, nitrilotriacetic acid, cyclohexanediaminetetraacetic acid, triethanolamine ethylenediaminetetraacetic acid, tetraethylenetriamine, ethylenediamine and diethylenetriamine, or a salt thereof.

* * * * *